United States Patent [19]

Koeneman

[11] Patent Number: 4,655,778
[45] Date of Patent: Apr. 7, 1987

[54] JOINT PROSTHESIS

[75] Inventor: James B. Koeneman, Mesa, Ariz.

[73] Assignee: Harrington Arthritis Research Center, Phoenix, Ariz.

[21] Appl. No.: 764,558

[22] Filed: Aug. 12, 1985

[51] Int. Cl.⁴ .............................................. A61F 2/42
[52] U.S. Cl. ........................................ 623/21; 623/18; 403/221; 403/225
[58] Field of Search ...................... 623/18, 19, 20, 21, 623/22, 23, 33, 35, 39, 47, 49; 403/158, 159, 162, 163, 221, 225

[56] References Cited

U.S. PATENT DOCUMENTS

| | | |
|---|---|---|
| 1,090,881 | 3/1914 | Rowley . |
| 1,911,440 | 5/1933 | Desoutter . |
| 2,011,817 | 8/1935 | Littlefield . |
| 2,183,076 | 12/1939 | Kaiser . |
| 2,605,475 | 8/1952 | Burger et al. . |
| 2,692,392 | 10/1954 | Bennington et al. . |
| 2,819,105 | 1/1958 | Behnke . |
| 3,147,963 | 9/1964 | Frazier . |
| 3,147,964 | 9/1964 | Wolf . |
| 3,462,765 | 8/1969 | Swanson . |
| 3,467,421 | 9/1969 | Bentley . |
| 3,480,972 | 12/1969 | Prahl . |
| 3,593,342 | 7/1971 | Niebauer et al. . |
| 3,707,006 | 12/1972 | Bokros et al. . |
| 3,875,594 | 4/1975 | Swanson . |
| 3,916,451 | 11/1975 | Buechel et al. . |
| 3,982,280 | 9/1976 | Asbelle et al. . |
| 3,986,212 | 10/1976 | Sauer . |
| 3,990,116 | 11/1976 | Fixel et al. . |
| 3,990,117 | 11/1976 | Pritchard et al. ............... 623/20 |
| 4,003,096 | 1/1977 | Frey ................................. 623/21 |
| 4,011,603 | 3/1977 | Steffee ............................. 623/21 |
| 4,038,705 | 8/1977 | Owens et al. . |
| 4,068,868 | 1/1978 | Ohrt . |
| 4,134,157 | 1/1979 | Laure . |
| 4,204,284 | 5/1980 | Koeneman . |
| 4,229,839 | 10/1980 | Schwemmer . |
| 4,279,041 | 7/1981 | Buchholz ..................... 623/23 X |
| 4,313,232 | 2/1982 | Habal et al. . |
| 4,352,212 | 10/1982 | Greene et al. . |

Primary Examiner—Richard J. Apley
Assistant Examiner—Alan W. Cannon
Attorney, Agent, or Firm—Wood, Herron & Evans

[57] ABSTRACT

A joint prosthesis for replacing a damaged or diseased joint between two or more skeletal members, including a distal joint component formed with a sleeve connected to a stem adapted to mount to one skeletal member, a proximal joint component having a housing connected to a stem adapted to mount to an adjoining skeletal member, and a hinge element comprising a hollow cylinder, a pin disposed within the cylinder and a layer of elastomeric material bonded therebetween. The joint components are pivotally interconnected by inserting the cylinder of the hinging element for rotation within the sleeve of the distal joint component, and fixing the ends of the pin of the hinging element to the housing of the proximal joint component so that the distal joint component is pivotal about the hinging element relative to the proximal joint component. The elastomeric material within the hinging element cushions the stems from shock, impact and lateral and compressive loads applied to the joint prosthesis to lessen the magnitude of the loads transmitted to the connection between the stems and skeletal members.

9 Claims, 5 Drawing Figures

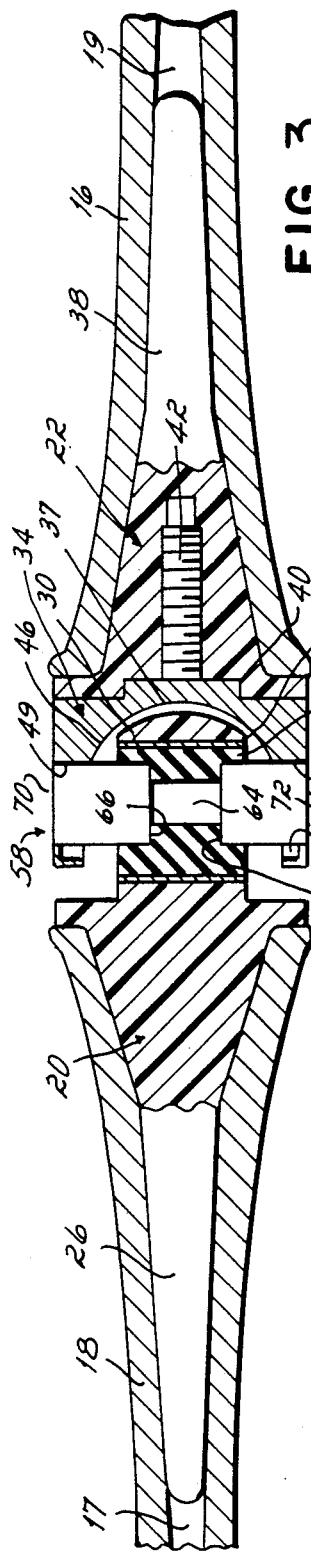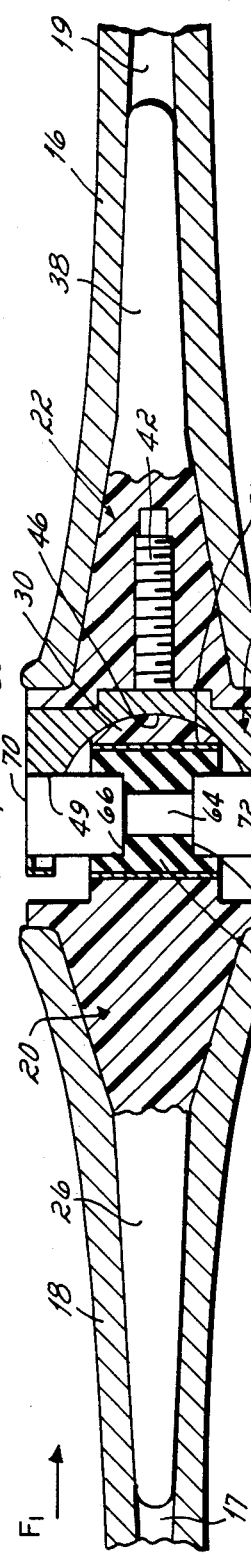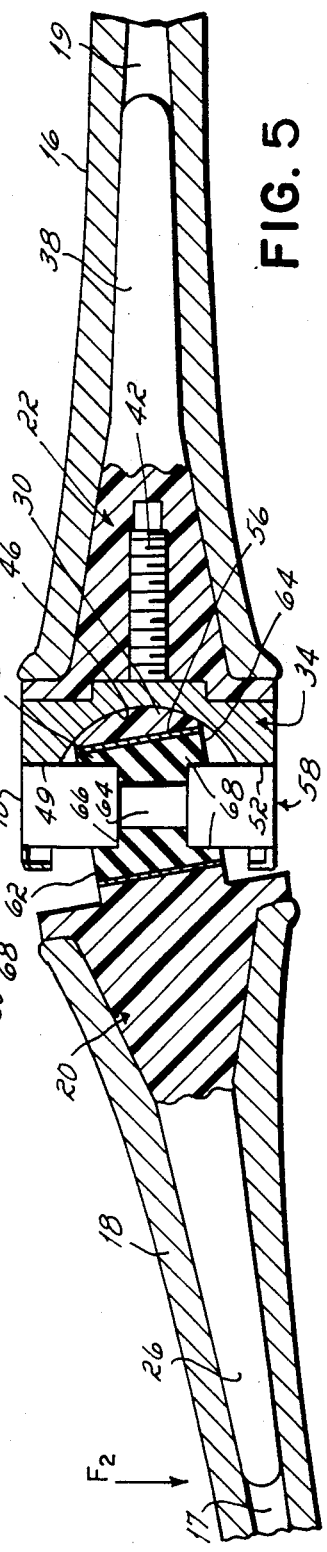

JOINT PROSTHESIS

BACKGROUND OF THE INVENTION

This invention relates to a joint prosthesis for replacing a diseased or damaged joint between skeletal members, and, more particularly, to a joint prosthesis having a durable, resilient hinging element.

The repair or complete replacement of damaged or diseased skeletal joints is a relatively common surgical procedure. Severe pain and restricted motion of skeletal joints caused by external trauma, rheumatoid arthritis and other conditions have been corrected by surgical procedures in which the skeletal joint is completely removed and replaced by a prosthesis extending into the intramedullary canals of the adjoining skeletal members. Several prior art prostheses for replacement of the fingers, toes, wrist, elbow, ankle and knee joints have been proposed, but problems have been encountered with each design.

One type of prior art prostheses design is exemplified in U.S. Pat. No. 4,352,212 to Greene et al which discloses a joint prosthesis for replacement of the metacarpophalangeal joint. This prosthesis includes one stem portion adapted for insertion into the intramedullary canal of a metacarpal bone and a second stem portion adapted for insertion into the intramedullary canal of a proximal phalanx. The stem portions are pivotally connected by a hinge construction in the form of a sleeve bearing which consists of a metal cylinder pivotal within a socket or cavity formed of rigid plastic or metal. Other prosthesis designs of this general type include a hinge construction for connecting the stem portions in the form of a ball bearing, usually having metal-to-metal bearing surfaces, such as shown in U.S. Pat. No. 4,304,011.

One problem with joint prostheses having hinging elements formed with metal-to-metal or metal-to-plastic bearing elements is that no resiliency or flexibility is provided at the hinging element to cushion and absorb impact loads, shock loads or lateral and compressive loads applied to the joint in everyday use. The stem portions of prostheses such as described in U.S. Pat. Nos. 4,352,212 and 4,304,011, are rigidly secured within the intramedullary canals of the adjoining skeletal members by bone cement, or with bone and tissue ingrowth induced by surface treatment of the stem portions or other known means. It has been found that the rigid metal-to-metal or metal-to-plastic connection of the members forming the hinging elements of such prior art prostheses fail to cushion or reduce the magnitude of impact or shock loads applied to the joint, but instead transmit them directly to the stem portions. These loads often break the engagement between the stem portions of the prosthesis and the bone cement or tissue ingrowth securing them in place within the intramedullary canals of the adjoining skeletal members. The prosthesis thus becomes loosened and dislocated within the skeletal members requiring replacement.

To avoid the rigid hinging connection between the stem portions of joint prostheses so that impact or shock loads are absorbed or cushioned, several designs have been proposed in which the prosthesis is formed almost entirely of a flexible material such as elastomer. This is particularly popular in finger joint prostheses such as shown, for example, in U.S. Pat. Nos. 3,462,765 to Swanson and 3,875,594 to Swanson. The Swanson finger joint is formed entirely of silicone rubber, preferably "Silastic" silicone elastomer which is a registered trademark of Dow Corning Corporation. The Swanson finger joint comprises a pair of silicone rubber stem portions adapted for insertion into the intramedullary canals of adjoining phalanges or a metacarpal bone and phalanx, which are connected by a section of silicone rubber to permit pivoting of the stem portions relative to one another. In the Swanson design, as well as other joint prostheses formed primarily of elastomer, the stem portions are not secured within the intramedullary canals but are movable and loosely fit within the adjoining skeletal members.

The Swanson type prosthesis employs a flexible hinging element between the stem portions within the intramedullary canals and thus provides better cushioning of loads applied to the prosthesis than prior art prostheses having rigid hinging elements. However, a new set of problems are created. Clinical trials have shown that the stem portions of the Swanson joint prosthesis often come completely out of the intramedullary canals of adjoining bones and must be reinserted in another surgical procedure. In addition, the elastomer stem portions and hinging section therebetween are so flexible that dislocation of one skeletal member relative to the adjoining skeletal member cannot be prevented. For example, one phalanx may be permitted to bend along an axis which is offset from the axis of an adjoining phalanx. This condition is common in advanced cases of rheumatoid arthritis. When adjoining phalanges are not aligned with one another, the stem portions are articulated along different axes when the fingers are bent causing a shear force to develop between the stem portions and the elastomer hinging element therebetween. Over a short period of time, this shear force causes the elastomer to tear resulting in complete failure of the prosthesis.

A third type of joint prosthesis has been developed to overcome the limitations of prior art designs, which is shown, for example, in U.S. Pat. No. 4,229,839. This patent discloses a joint prosthesis whose stem portions are adapted to be fixed within the intramedullary canals of the adjoining skeletal members, and whose hinge element provides a resilient connection between the stem portions. The hinging element consists of a rigid pin which is connected to one stem portion by a first body of elastomer and to the other stem portion by a second body of elastomer. The bodies of elastomer help to reduce the magnitude of loads transmitted to the stem portions and, in turn, their connection to the intramedullary canals of the adjoining skeletal members.

One problem with this design is that the bending of one skeletal member relative to the other requires the elastomer bodies to be bent or flexed at their connection to the pin and/or stem portions. In order to accommodate the millions of bending motions which normal skeletal joints undergo, an elastomeric material having a high flex life must be utilized which adds to the expense and difficulty of manufacturing the prosthesis. A second problem with this design is that it is subject to failure where the adjoining skeletal members are articulated or loaded along offset or non-aligning axes. The joint prosthesis may be subjected to off-axis loading or movement where the stem portions are not precisely aligned with the longitudinal axes of the skeletal members in which they are attached, or where the skeletal members themselves do not anatomically align as a result of an arthritic condition or some external trauma. If the stem portion connected to one body of elastomer is not aligned with the stem portion connected to the other body of elastomer, one of the elastomer bodies will be subjected to shear forces when the prosthesis is articulated. Over time, these shear forces can create tears in the elastomer bodies resulting in complete failure of the prosthesis.

SUMMARY OF THE INVENTION

It is therefore among the primary objects of this invention to provide a joint prosthesis for the replacement of an entire joint between adjoining skeletal members which is adapted to be fixed within the intramedullary canals of the adjoining skeletal members to aid in aligning the skeletal members in the correct anatomical position, which includes a flexible, resilient hinging element capable of reducing the magnitude of impact loads and compressive and lateral loads applied to the stem portions attached within the adjoining skeletal members, which includes a durable, inexpensive and easily manufactured hinging element, and which is substantially fail-safe in operation.

These objectives are accomplished in a joint prosthesis which comprises a distal joint component and a proximal joint component interconnected by a resilient hinging element. For purposes of describing the invention, the joint prosthesis herein is designed to replace the metacarpophalangeal joint between one of the metacarpal bones and a proximal phalanx. However, the joint prosthesis may be utilized in replacing a number of other skeletal joints as described below.

The distal joint component is formed of plastic and includes a stem portion adapted for insertion into the intramedullary canal of the proximal phalanx. The opposite end of the distal joint component includes a sleeve formed with a bore extending transverse to the axis of the stem. The proximal joint component is formed with a plastic stem portion adapted for insertion into the intramedullary canal of the adjoining metacarpal, which is connected to a metal housing formed with a cavity. The hinging element comprises a hollow metal cylinder, a metal pin disposed within the cylinder so that its ends extend outwardly from the cylinder, and a layer of resilient material such as elastomer mounted between the cylinder and pin. The cylinder is insertable within the bore formed in the sleeve of the distal joint component. The diameter of the cylinder is less than the bore to permit rotation of the cylinder within the sleeve. The ends of the pin are fixed within the cavity of the proximal joint component to connect the distal and proximal joint components. Articulation of the joint prosthesis is therefore permitted by rotation of the distal joint component about its sliding connection to the cylinder of the hinging element which is fixed to the proximal joint component.

Preferably, the distal joint component and stem portion of the proximal joint component are formed of a low modulus thermoplastic acetal resin such as Delrin plastic, which is a registered trademark of E. I. duPont de Nemours & Co. The cylinder and pin of the hinging element, and the housing of the proximal joint component, are preferably formed of cobalt-chrome, stainless steel or titanium. These materials are biocompatible, durable, and provide sufficient support for proper anatomical positioning of the adjoining skeletal members.

In a presently preferred embodiment of this invention, the outer surface of the cylinder forming the hinging element includes spaced, axially extending grooves which are adapted to capture any wear debris which may be produced as the sleeve in the distal joint component slides about the cylinder. In addition, the pin of the hinging element is formed with at least one offset section or shoulder to create a mechanical engagement between it and the surrounding elastomer, which is also bonded to the pin with adhesives or by vulcanization. The metal housing of the proximal joint component preferably includes a threaded projection adapted to seat within a mating bore formed in its plastic stem section for mounting the housing to the stem section.

One advantage of this invention is that the stem portions of the distal and proximal joint components are fixed within the intramedullary canals of the adjoining skeletal members by bone cement or tissue ingrowth. This eliminates the problem of stem dislocation which can occur in some joint prostheses formed entirely of resilient material whose stems are loosely fitted into the intramedullary canals of adjoining skeletal members.

Another important advantage of this invention is that the hinging element cushions the connection between the joint components and adjoining skeletal members, but resists failure under load or due to repetitive articulation of the joint over a long period of time. Unlike the joint prosthesis having pivoting elastomer bodies as disclosed in U.S. Pat. No. 4,229,839 issued to Schwemmer, normal articulation of the skeletal members in this invention is accommodated by rolling or sliding contact of the cylinder of the hinging element with the sleeve formed in the distal joint component. In the Schwemmer patent, every flexure of the skeletal members causes bending of the elastomer bodies forming the hinging element. In contrast, in a joint prosthesis according to this invention, the elastomer layer within the hinging element remains substantially unloaded during normal articulation of the skeletal members.

Under the application of compressive or lateral loads to the skeletal members, the elastomer layer within the hinging element of this invention is subjected to primarily compressive forces. As is well known, elastomer has high compressive strength. For example, if the skeletal members are subjected to compressive load so that the distal and proximal joint components are urged toward one another, the elastomer layer is compressed within the cylinder of the hinging element. If a heavy compressive load is applied, the elastomer layer is compressed until the sleeve of the distal joint component engages the cavity formed in the housing of the proximal joint component, permitting no further compression of the elastomer layer. Under the application of a lateral load wherein one joint component tends to be cocked or forced at an angle relative to the other, the elastomer layer undergoes a combination of tensile and compressive loading, as the pin fixed to the proximal joint component pivots against the elastomeric layer within the cylinder contained in the sleeve of the distal joint component. The tensile and compressive loading applied to the elastomer layer under the application of lateral loads is limited by the presence of the surrounding metal cylinder. Engagement of the sleeve of the distal joint component within the housing of the proximal joint component protects the elastomer layer if high lateral loads are applied.

Since the elastomer layer of the hinging element is not stressed under normal articulation of the skeletal members, and is protected from heavy compressive or lateral loads by the surrounding cylinder member and engagement of the distal and proximal joint components, the elastomer layer in this invention is much less subject to failure than elastomeric material used in hinging elements of prior art joint prosthesis. In addition, a less expensive, readily available elastomer may be used in forming the hinging element as compared to the high flex life elastomer required in prior art joint components such as shown in the U.S. Pat. No. 4,229,839.

One further advantage of this invention over prior art joint prostheses having flexible hinging elements is that failure of the elastomer layer within the hinging element does not cause complete failure of the prosthesis. The cylinder member of the hinging element is rotatable within the sleeve of the distal joint component to permit articulation of the adjoining skeletal members even if the elastomer layer should fail. All that is lost with failure of the elastomer layer is the resiliency provided by the hinging element, which would not require replacement of the prosthesis. This feature thus adds a fail-safe aspect to this invention, at least with respect to permitting continued articulation of the skeletal members.

DESCRIPTION OF THE DRAWINGS

The structure, operation and advantages of this invention will become further apparent upon consideration of the following description taken in conjunction with the accompanying drawings, wherein:

FIG. 3 is a partial cross sectional view of the joint prosthesis of this invention in an unstressed condition;

FIG. 4 is the joint prosthesis of FIG. 3 under the application of a compression load; and FIG. 5 is the joint prosthesis of FIG. 3 under the application of a lateral load.

DETAILED DESCRIPTION OF THE INVENTION

Figure 1:
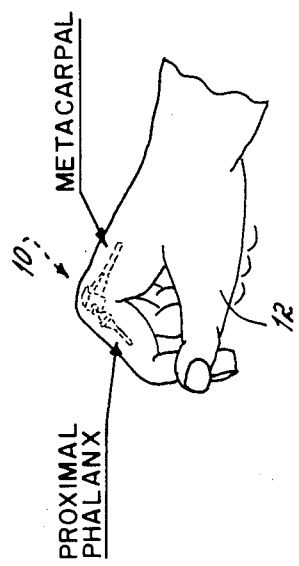
FIG. 1 is a schematic, perspective view of a hand in which the joint prosthesis of this invention shown replacing a metacarpophalangeal joint.
Figure 2:
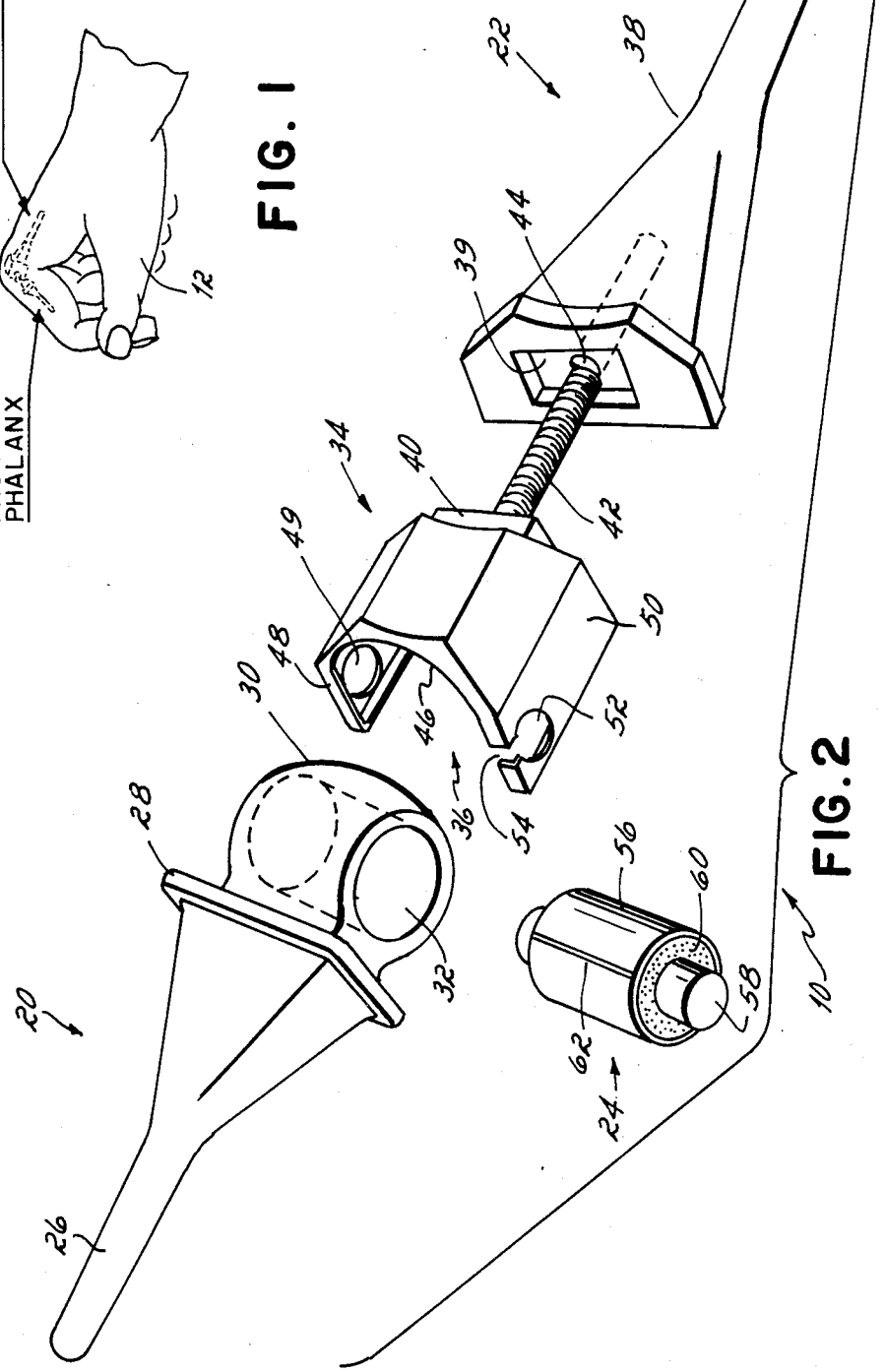
FIG. 2 is an exploded, perspective view of the joint prosthesis shown in FIG. 1.

Referring now to the figures, a joint prosthesis 10 is shown schematically in position within a hand 12 replacing the metacarpophalangeal joint between a metacarpal 16 and a proximal phalanx 18. The joint prosthesis 10 herein is shown replacing a metacarpophalangeal joint for purposes of illustrating and discussing the structure and advantages of this invention. It should be understood, however, that the joint prosthesis 10 may also be used to replace the joints between the phalanges of the fingers and toes, and the elbow, wrist, shoulder, knee and ankle joints. It is contemplated that some modification of the joint prosthesis 10 would be required for replacement of joints other than the metacarpophalangeal joint shown in the drawings, but such modification would be in the nature of accommodating the particular size and anatomical position of the skeletal members connected by the natural joint to be replaced, without changing the essential structure of this invention.

The joint prosthesis 10 comprises a distal joint component 20, a proximal joint component 22 and a hinge element 24 for pivotally interconnecting the distal and proximal joint components 20, 22.

As used hereinafter to describe the materials forming the joint prosthesis 10, the term "plastic" refers to a low modulus thermoplastic acetal resin sold under the registered trademark "Delrin" owned by E. I. duPont de Nemours & Co., an ultra high molecular weight polyethylene or fiber filled polyethylene. The "metal" components of this invention are preferably a cobalt-chrome alloy, titanium or 316 stainless steel. The "elastomer or rubber" components are preferably any one of a number of commercially available urethane elastomers or silicon rubber.

The distal joint component 20 is a one-piece molded plastic element including a stem 26 having a flange 28 at one end connected to an annular sleeve 30 formed with a bore 32 extending transverse to the axis of stem 26. The stem 26 of distal joint component 20 is insertable within the intramedullary canal 17 of the proximal phalanx 18, and secured therein by bone cement (not shown), or other known methods of fixation such as tissue and bone ingrowth.

The proximal joint component 22 comprises a metal housing 34 connected to a molded plastic stem 38. The stem 38 is connected by bone cement or tissue ingrowth within the intermedullary canal 19 of the metacarpal 16. The metal housing 34 includes a cavity 36 formed with a polished arcuate surface 46 and a pair of spaced arms 48, 50 disposed on either side of the arcuate surface 46. A bore 49 is formed in arm 48, and a bore 52 connected to a radially outwardly extending slot 54 is formed in the arm 50. Preferably, the metal housing 34 is formed with a shoulder 40 having a threaded projection 42 extending outwardly therefrom. The projection 42 is insertable within a bore 44 formed in the plastic stem 38, which is formed with a recess 39 adapted to mate with the shoulder 40 of the housing 34. The projection 42 may be sized to press fit within the bore 44 of stem 38 to secure the housing 34 to the stem 38. Alternatively, the projection 42 is first sized to create an interference fit when inserted within the bore 44, and then welded ultrasonically to the stem 38 so that the plastic from the interior of stem 38 is melted around the threads of the projection 42. It is also contemplated that the housing 34 and stem 38 could be connected in a molding operation wherein the housing 34 is placed in a mold and the plastic forming stem 38 is molded about the shoulder 42 and threaded projection 40 of the housing 34.

The distal joint component 20 is pivotally connected to the proximal joint component 22 by the hinge element 24. The hinge element 24 comprises a metal cylinder 56, a metal pin 58 disposed within the cylinder 56 and a layer of elastomer 60 disposed between and bonded to the cylinder 56 and pin 58. The elastomer layer 60 is connected to the cylinder 56 and pin 58 by suitable rubber-to-metal adhesives or vulcanization. Preferably, the pin 58 is irregular in shape having a center section 64 connected to radially outwardly extending shoulders 66, 68 having mounting ends 70 and 72, respectively. See FIGS. 3-5. The shoulders 66, 68 engage the elastomer layer 60 and help resist separation of the pin 58 from elastomer layer 60, in addition to the adhesive bond therebetween. The cylinder 56 is formed with spaced grooves 62 extending axially along its exterior surface.

To interconnect the distal and proximal joint components 20, 22, the hinge element 24 is first inserted into the bore 32 formed in the annular sleeve 30 of distal joint component 20. The cylinder 56 has a smaller diameter than the bore 32 so that it freely rotates therewithin, and the mounting ends 70, 72 of pin 58 extend outwardly from the sleeve 30. The sleeve 30 of distal joint component 20 is then placed within the cavity 36 in housing 34 of proximal joint component 22 so that the mounting end 70 of pin 58 extends within the bore 49 formed in the arm 48 of housing 34. The mounting end 72 on the opposite side of pin 58 is then urged through the slot 54 and into the bore 52 formed in the arm 50 of housing 34. The pin 58 is fixed within the bores 49, 52 of proximal joint component 22 by welding each mounting end 70, 72 to the housing 34 or crimping the slot 54 to secure mounting end 72 within the bore 52. Preferably, when the joint components 20, 22 are connected, the sleeve 30 of distal joint component 20 is disposed a space 37 from the arcuate surface 46 formed in the cavity 36 of proximal joint component 22.

Several advantages provided by the joint prosthesis 10 of this invention may be best appreciated with reference to its operation under unloaded and loaded conditions. Referring now to FIG. 3, the joint prosthesis 10 is shown schematically in an unloaded condition. In this position, the sleeve 30 of distal joint component 20 is disposed a space 37 from the arcuate surface 46 of the cavity 36 formed in proximal joint component 22. If the proximal phalanx 18 is pivoted relative to the metacarpal 16 while applying little or no load to the joint prosthesis 10, the distal joint component 20 pivots relative to the proximal joint component 22 by sliding motion of its sleeve 30 about the cylinder 56 of hinge element 24 which is fixed to the proximal joint component 22. The elastomer layer 60 within the hinge element 24 is unstressed and little or no stress is applied between the cylinder 56 and sleeve 30 as they slide relative to one another.

It is contemplated that much of the flexing motion at the metacarpophalangeal joint 14, or for that matter the interphalangeal joints in the fingers, is performed under minimal loading conditions. However, the hinge element 24 interconnecting the distal and proximal joint components 20, 22 must provide a cushioning effect when loads are applied to skeletal joints so that the magnitude of the loads are at least reduced before being transmitted to the joint components 20, 22 and their connections to the intramedullary canals 17, 19. In FIG. 4, the joint prosthesis 10 is subjected to a compressive load which could be caused, for example, by impact of the finger with a solid object. When a compressive load $F_1$ is applied to the joint prosthesis 10, the elastomer layer 60 within hinge element 24 is compressed within the cylinder 56. This is because the distal joint component 20 is urged toward the proximal joint component 22 which presses the elastomer layer 60 against the fixed pin 58. The elastomer layer 60 absorbs at least a portion of the load to reduce its magnitude and cushion the distal and proximal joint components 20, 22. If a large compressive load is applied, as illustrated in the drawing, the sleeve 30 of distal joint component 20 engages the arcuate surface 46 of proximal joint component 22 to prevent overloading of the elastomer layer 60. Preferably, the space 37 between sleeve 30 and arcuate surface 46 in the unstressed position of prosthesis 10 is such that the elastomer layer 60 is permitted to be compressed to a limited degree, well within its ultimate compressive strength, before sleeve 30 engages arcuate surface 46.

Application of a lateral load $F_2$ to the joint prosthesis 10 is shown in FIG. 5, which is greatly exaggerated for purposes of illustration. This could occur when one or the other of the metacarpals 16 or proximal phalanx 18 is stressed such as by lifting an object with the fingers in a fixed position. In accommodating lateral loads, the elastomer layer 60 undergoes both tension and compression because sleeve 30 is cocked or angled relative to the fixed pin 58 as the distal joint component 20 moves at an angle relative to the longitudinal axis of the proximal joint component 22. Portions of the elastomer layer 60 on one side of the pin 58 shown at 62 and 64 are subjected to tensile forces as they tend to be pulled away from the inner wall of the cylinder 56, but these forces are resisted as portions of the elastomer layer 60 shown at 66 and 68 are compressed against the inner wall of the cylinder 56. The elastomer layer 60 thus imparts a cushioning effect to the distal and proximal joint components 20, 22 without undergoing substantial deformation or tensile stresses which could create failure. In addition, larger lateral loads cause the sleeve 30 to move across the space 37 and engage the arcuate surface 46 of proximal joint component 22 to further protect the elastomer layer 60 in the same manner as described above for compressive loads.

By confining the cushioning elastomer layer 60 within a rigid cylinder 56 and providing for the carrying of larger lateral and compressive loads by the engagement of sleeve 30 with arcuate surface 46, the joint prosthesis 10 of this invention provides a hinge element 24 which effectively cushions the joint components 20, 22 and yet is extremely durable over long periods of use. The durability of joint prosthesis 10 is further enhanced by the provision of grooves 62 in cylinder 56 which act to capture any wear debris (not shown) which could be produced by the sliding motion between the metal cylinder 56 and plastic sleeve 30.

Even if the elastomer layer 60 should fail, articulation of the proximal phalanx 18 relative to the metacarpal 16 would still be permitted by the pivotal connection between the cylinder 56 of hinge element 24 fixed to the proximal joint component 22 and the sleeve 30 of distal joint component 20. This provides a fail-safe feature of the joint prosthesis 10 herein because only a portion of the original cushioning ability of the hinge element 24 is lost with a failure of elastomer layer 60 with the joint prosthesis 10 being otherwise fully operational.

While the invention has been described with reference to a preferred embodiment, it will be understood by those skilled in the art that various changes may be made and equivalents may be substituted for elements thereof without departing from the essential scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims.

I claim:

1. A joint prosthesis for replacing the joint between at least two skeletal members, comprising:
   a first joint component having a stem portion adapted to mount to one of said skeletal members;
   a second joint component having a stem portion adapted to mount to at least one of said other skeletal members;
   a hinging element including a hollow cylinder having an inside surface and an outside surface, and a section of resilient material mounted to said inside surface of said cylinder;
   means for pivotally mounting said first joint component to said outside surface of said hollow cylinder;

means for mounting said second joint component to said section of resilient material, said first joint component being pivotal relative to said second joint component to permit articulation of one skeletal member relative to at least one other skeletal member.

2. The joint prosthesis of claim 1 in which said means for mounting said second joint component to said section of resilient material is a pin mounted within said section of resilient material, said section of resilient material being disposed between said pin and said inside surface of said hollow cylinder.

3. The joint prosthesis of claim 2 in which said pin is fixedly mounted to said second joint component.

4. A joint prosthesis for replacing the joint between at least two skeletal members, comprising:
 a distal joint component including a stem portion and a sleeve, said stem portion being adapted to attach to one of the skeletal members;
 a proximal joint component formed with a stem portion adapted to attach to at least one of the other skeletal members;
 a hinging element comprising a hollow cylinder having an inside surface and an outside surface, a section of elastomeric material mounted to said inside surface of said hollow cylinder and a pin fixedly mounted within said section of elastomeric material;
 said hinging element being insertable within said sleeve of said distal joint component so that said sleeve is pivotal with respect to said outside surface of said cylinder;
 means for fixedly mounting said pin of said hinging element to said proximal joint component, said distal joint component thereby being pivotal relative to said proximal joint component to permit articulation of one of the skeletal members relative to at least one other skeletal member.

5. The joint prosthesis of claim 4 in which said distal joint component is a one-piece section of molded plastic formed with a stem portion adapted to mount within the intramedullary canal of one of the skeletal members, and a sleeve formed with a bore extending substantially perpendicularly to the axis of said stem.

6. The joint prosthesis of claim 4 in which said proximal joint component comprises:
 a one-piece section of plastic material formed with a stem portion, a recess and a bore extending substantially perpendicularly to said recess;
 a hollow metal housing including a pair of spaced arms defining an internal cavity having a spherical-shaped surface, said hollow metal housing being formed with an outwardly extending shoulder connected to a projection;
 said one-piece section of plastic material being connected to said metal housing so that said projection of said metal housing is mounted within said bore of said one-piece section and said shoulder of said metal housing is mounted within said recess formed in said one-piece section.

7. The joint prosthesis of claim 4 in which said outside surface of said hollow cylinder of said hinging element is formed with at least one axially extending groove for collecting wear debris.

8. The joint prosthesis of claim 4 in which said pin is formed in an irregular shape for engagement with said elastomeric material.

9. The joint prosthesis of claim 6 in which each of said spaced arms of said hollow metal housing is formed with means for mounting to an end of said pin of said hinging element.

* * * * *